United States Patent
Hsieh

[19]

[11] Patent Number: 6,035,012
[45] Date of Patent: Mar. 7, 2000

[54] ARTIFACT CORRECTION FOR HIGHLY ATTENUATING OBJECTS

[76] Inventor: Jiang Hsieh, 19970 W. Keswick Ct., Brookfield, Wis. 53045

[21] Appl. No.: 09/078,938

[22] Filed: May 14, 1998

[51] Int. Cl.$^7$ ........................................................ A61B 6/03
[52] U.S. Cl. ................................. 378/4; 378/8; 378/901
[58] Field of Search ........................... 378/4, 8, 901; 382/131

[56] References Cited

U.S. PATENT DOCUMENTS

| | | | |
|---|---|---|---|
| 4,626,991 | 12/1986 | Crawford et al. | 378/4 |
| 5,412,703 | 5/1995 | Goodenough et al. | 378/8 |
| 5,727,041 | 3/1998 | Hsieh | 378/4 |

*Primary Examiner*—David Vernon Bruce
*Attorney, Agent, or Firm*—John S. Beulick; Christian G. Cabou; Phyllis Y. Price

[57] ABSTRACT

The present invention, in one form, is a method for correcting for artifacts caused by highly attenuating objects in a CT image data using a correction algorithm. In accordance with one embodiment of the algorithm, the highly attenuating objects are identified in the image data using the CT numbers from the image data. The segmented image data for each highly attenuating material are used to produce separate component images for each material. The component image data for each material is then separately forward projected to generate projection data for each material. The projection data for each material is then adjusted for the attenuation characteristic of the material to generate projection error data for each material. The resulting projection error data are then filtered and backprojected to produce error-only image data. The error-only image data are then scaled and combined with the original image data to remove the highly attenuating object artifacts.

29 Claims, 2 Drawing Sheets

ARTIFACT CORRECTION FOR HIGHLY ATTENUATING OBJECTS

FIELD OF THE INVENTION

This invention relates generally to computed tomography (CT) imaging and more particularly, to correcting for highly attenuating object artifacts in a CT scan image.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed. In addition to reduced scanning time, helical scanning provides other advantages such as improved image quality and better control of contrast.

In helical scanning, and as explained above, only one view of data is collected at each slice location. To reconstruct an image of a slice, the other view data for the slice is generated based on the data collected for other views. Helical reconstruction algorithms are known, and described, for example, in C. Crawford and K. King, "Computed Tomography Scanning with Simultaneous Patient Translation," Med. Phys. 17(6), November/December 1990.

In general, highly attenuating objects such as bones and metal objects produce beam hardening, partial volume, or under-range in the data acquisition electronics. These effects, in turn, produce shading or streaking artifacts. For example, titanium braces often are used on patients undergoing spine surgery. In one configuration, the brace is placed in the invertebral space so that the bone is allowed to grow within the titanium brace. In order to monitor progress of the patient, bone growth must be monitored within the brace. With known CT scanners, however, the metal artifact induced by the titanium brace is quite severe and a significant CT number shift occurs. As a result, monitoring the amount of bone growth within the brace is difficult.

It would be desirable to correct for artifacts caused by highly attenuating objects. It also would be desirable to correct for such artifacts without significantly increasing the cost of the system.

SUMMARY OF THE INVENTION

These and other objects may be attained by a correction algorithm that corrects for highly attenuating object artifacts. In accordance with one embodiment of the present invention, the patient is scanned to generate projection data. The projection data is processed to generate image data. The image data is then processed to identify highly attenuating objects. Such identification is performed by segmenting the image data into highly attenuating material classes. The material classes include each type of highly attenuating material that is expected for a specific scan. The image data is segmented by assigning each CT number to a particular class. For example, for a titanium brace, the each CT number is segmented in the expected material classes of bone, soft-tissue, and titanium.

Separate component image data is then generated for each highly attenuating material. Particularly, the image data is multiplied by a membership function for each highly attenuating material. Projection error data is generated using an attenuation characteristic function. The attenuation characteristic function represents the total amount of attenuation for various thicknesses of the highly attenuating material.

Error-only image data is generated for each highly attenuating material by filtering and backprojecting the projection error data. The error-only image data is then scaled and combined with the original image data to correct for the artifacts caused by the highly attenuating objects. The combined data is processed to produce a corrected image that may be displayed.

The above described algorithm corrects for artifacts caused by highly attenuating objects. As a result, with highly attenuating objects, improved images can be generated. dr

DETAILED DESCRIPTION

Figure 1:
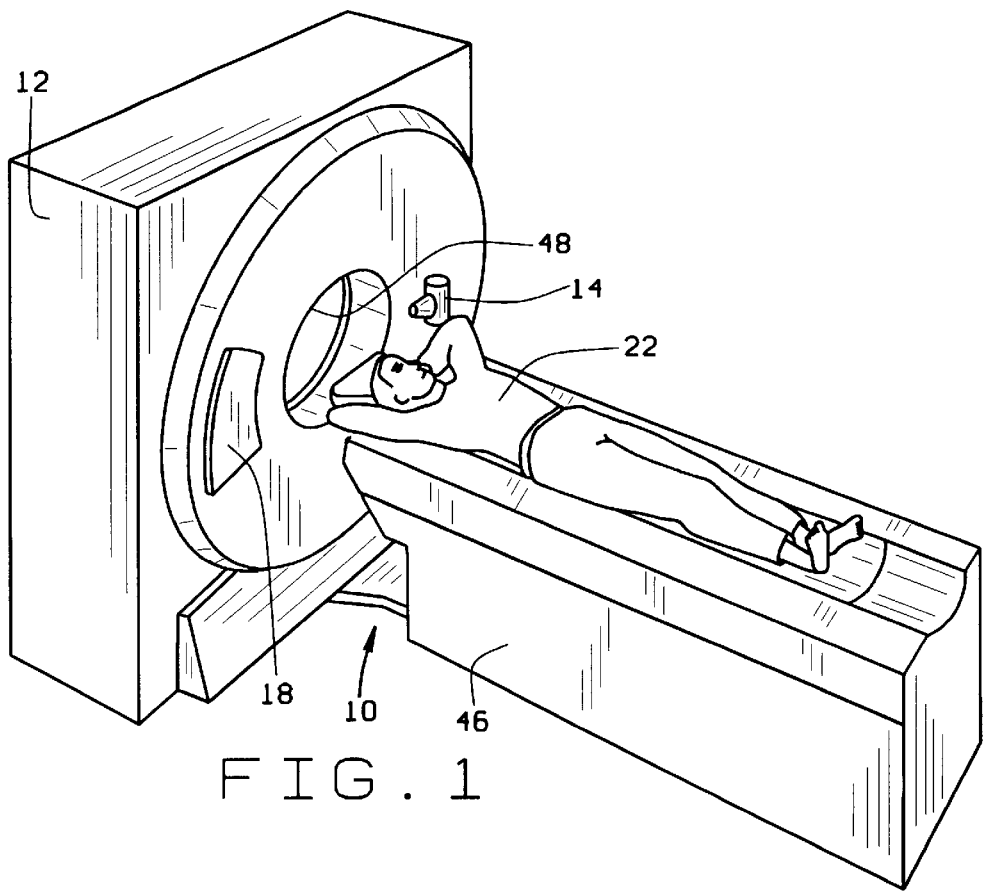
FIG. 1 is a pictorial view of a CT imaging system.
Figure 2:
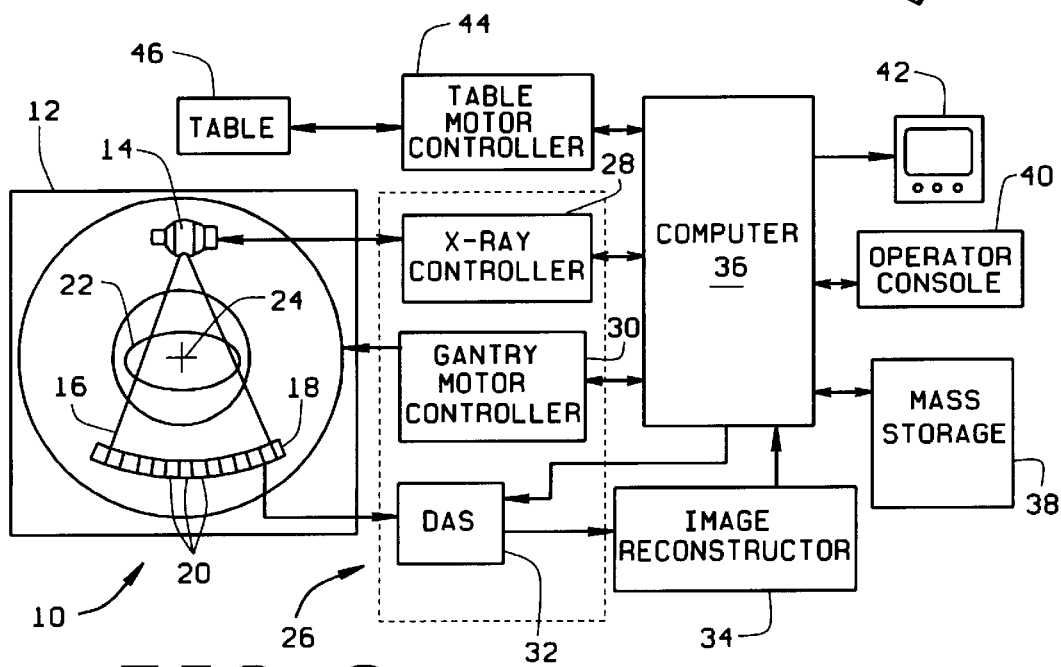
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. X-ray beam is collimated by a collimate (not shown) to lie within in an X-Y plane of a Cartesian coordinate system and generally referred to as an "imaging plane". Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The following discussion which describes correcting for highly attenuating object artifacts sometimes refers specifically to an axial scan. The artifact correction algorithm, however, is not limited to practice in connection with only axial scans, and may be used with other scans, such as helical scans. It should be further understood that the algorithm described below may be implemented in computer 36 and would process, for example, reconstructed image data. Alternatively, the algorithm could be implemented in image reconstructor 34 and supply corrected image data to computer 36. Other alternative implementations are, of course, possible. In addition, the term "highly attenuating" objects refers to those objects of a material having significantly different densities as compared to soft tissue.

As described above, in performing a CT scan, data from detector elements 20 is obtained. Such data is generally referred to in the art as projection data. High speed image reconstruction is then performed to generate image data. With respect to image reconstruction, many image reconstruction algorithms currently are implemented in commercially available CT machines and the present image correction algorithm could be implemented in connection with many of such reconstruction algorithms.

In accordance with one embodiment of the present invention, image data is corrected for highly attenuating object artifacts by identifying each highly attenuating object, generating error-only image data for each highly attenuating material, and combining the error-only image data with the original image data to generate corrected image data. The corrected image data is then processed to generate a corrected image.

Prior to identifying the highly attenuating objects, attenuation characteristics for commonly encountered highly attenuating materials are determined. Specifically, an attenuation characteristic for each material is determined, or characterized, by measuring the amount of attenuation for various thicknesses of the material. The measured attenuation is plotted against the material thickness to generate an attenuation curve. An attenuation characteristic function is then determined using the attenuation curve using known curve fitting algorithms.

Figure 3:
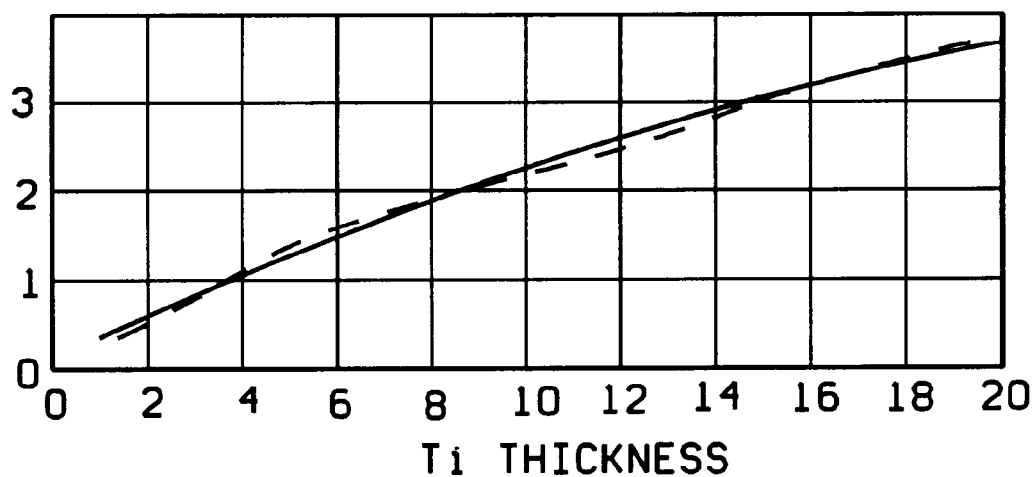
FIG. 3 is an attenuation characteristic plot of a highly attenuating material.

For example, and referring to FIG. 3, using a second order fit, the attenuation characteristic of titanium is:

$$\lambda = 0.16602 + 0.23334 1t - 0.00290 t^2$$

where: $\lambda$=total amount of attenuation
t=thickness of titanium (Ti).

Subsequent to determining an attenuation characteristic for each material, the highly attenuating objects are identified in the image data. This identification is performed by initially identifying the material that is contained in the image data. The highly attenuating material identification is based on the type of scan being performed. For example, if performing a dental scan with tooth fillings, the highly attenuating objects are identified, typically, as mercury. Following identification of the materials, the image data is segmented into separate classes and corrected. Specifically, the image data is separate into a separate class for each highly attenuating material that has been identified. For example, when scanning the titanium brace described above, the image data is segmented into three separate classes, namely, soft-tissue, bone, and titanium. Depending upon the test to be performed additional classes may be defined.

To perform the segmentation, CT numbers from the image data are used. Particularly, each CT number in the image data is assigned to a certain class based on its intensity. In general, different materials have different CT numbers. For example, bone has a CT number of over 200, water has a CT number of 0, soft-tissue (in the brain) has a CT number from approximately 20–50, and air has a CT number of −1000. Since the CT numbers are different for various materials, a thresholding method can generally be used to assign CT numbers to certain classes, e.g., water and soft-tissue. Many thresholding methods are known in the art.

Figure 4:
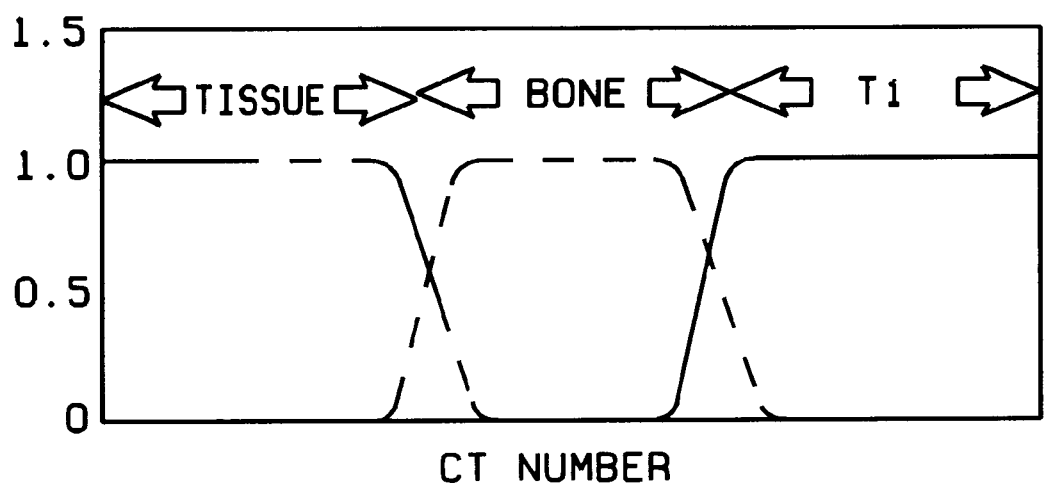
FIG. 4 illustrates membership functions of soft-tissue, bone, and titanium.

As shown in FIG. 4, many CT numbers, however, have intensities which fall between classes, or thresholds. To assign such CT numbers to appropriate classes, fuzzy logic can be used to generate a membership function for each material. For example, some CT numbers cannot be assigned, with great confidence, either to bone or to titanium. Such CT numbers have a dual membership to both the bone class and the titanium class. Utilizing fuzzy logic, the CT number may be determined to belong to titanium class with a first membership grade, and belong to bone class with a second membership grade. The transition function from the bone region to the titanium region can be either linear or non-linear functions.

In one embodiment shown in FIG. 4, as the CT number increases, the membership grade for tissue decreases and the membership grade for bone increases. When the CT number is high, the CT number membership grade transitions from bone to titanium. The membership functions are designed so that the materials are properly excluded from the other classes.

Next, component image data is generated for each highly attenuating material. Specifically, the image data is multiplied by the membership function of each highly attenuating material. For example, when scanning the titanium brace, the reconstructed image data will be multiplied by the bone membership function to generate bone-only component image data. In addition, the image data will be multiplied by the titanium membership function to generate titanium-only component image data.

The bone-only component image data and titanium-only component image data are then separately forward projected to produce sets of bone projection data and titanium projection data. Forward projecting techniques are known, and many techniques may be used in connection with the present algorithm. The forward projecting produces smoother projections due to the interpolation process. The bone and titanium projection data are then adjusted using the attenuation characteristic function to generate separate bone and titanium projection error data. Specifically, the bone projection data is adjusted according to the bone attenuation characteristic function and the titanium projection data is adjusted for the to the titanium attenuation characteristic function.

In an alternative embodiment, for those scans containing sharp images, the reconstructed image data may be produced with a higher cut-off frequency to produce the component image data. In another alternative, the original reconstructed image data may be filtered using high filters to generate edge enhanced image data.

After filtering the bone and titanium projection error data, the resulting filtered data is backprojected to produce error-only image data for each material. The error-only image data for each material are scaled and added to the original image data to correct for the highly attenuating object artifacts. After combining the error-only data and the image data, the resulting data is processed to produce a corrected image. The corrected image is then displayed, for example, on display 42.

In an alternative embodiment, the attenuation characteristic for the highly attenuating materials may be adjusted based on the image data collected from neighboring slices. Specifically, assuming that the attenuation characteristic of the highly attenuating object does not change very quickly, the attenuation characteristic is adjusted to maximize the uniformity of the surrounding areas after the image data is corrected for highly attenuating objects. The attenuation characteristics may be adjusted any number of times to ensure overall performance of the correction. In addition, the intensity of a region, or slice, immediately next to the highly attenuating object may be compared to the intensity of a region, or slice a small distance away from the highly attenuating object. If the variation between the immediate neighbor and the surrounding area is larger than a first threshold, no correction is applied. However, if the variation is within a valid range of smaller than the first threshold but larger than a base threshold, the attenuation characteristic of the highly attenuating material may be adjusted so that the corrected image data reflects a flat intensity.

In another alternative embodiment, the operator may select from a set of pre-defined, or pre-stored, attenuation characteristics based on information provided by patient 22 or the patient's medical record. These pre-stored attenuation characteristics represent commonly encountered highly attenuating materials. If information related to the specific highly attenuating objects is unavailable, the attenuation characteristics will be selected based on the type of scan to be completed, e.g., for a dental scan the highly attenuating material is most likely mercury.

In a further alternative embodiment, the projection data for each material may be combined prior to being filtered and backprojected. The combined projection data is then processed as described above. Such processing may improve the speed at which the corrected image is generated.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

I claim:

1. A method of correcting for artifacts caused by highly attenuating objects in image data, the image data collected in a computed tomography system, said method comprising the steps of:

determining an attenuation characteristic for each highly attenuating material of the highly attenuating objects;

identifying the highly attenuating objects in the image; and generating error-only image data for each highly attenuating object.

2. A method in accordance with claim 1 wherein identifying the highly attenuating objects comprises the steps of:

segmenting the image data into material classes; and generating a membership function for each material class.

3. A method in accordance with claim 1 wherein generating error-only image data for each highly attenuating object comprises the step of generating separate component image data for each highly attenuating material.

4. A method in accordance with claim 3 wherein generating separate component image data comprises the step of multiplying the image data by each material class membership function.

5. A method in accordance with claim 3 wherein generating error-only image data for each highly attenuating object further comprises the steps of:

generating projection data by forward projecting the component image of each highly attenuating material; and generating projection error data by adjusting the projection data.

6. A method in accordance with claim 5 wherein generating projection error data by adjusting the projection data comprises the step of adjusting the projection data by the attenuation characteristic of each highly attenuating material.

7. A method in accordance with claim 6 wherein adjusting the projection data by the attenuation characteristic of each highly attenuating material comprises the steps of:

using operator supplied data to identify the highly attenuating materials; and adjusting the projection data by pre-defined attenuation characteristics based on the identified highly attenuating materials.

8. A method in accordance with claim 7 wherein using the operator supplied data to identify the highly attenuating materials comprises the step of identifying the type of scan to be performed.

9. A method in accordance with claim 5 wherein generating error only image from the projection data comprises the steps of:

filtering the projection error data for each highly attenuating material; and backprojecting the filtered projection error data.

10. A method in accordance with claim 5 further comprising the step of combining the projection data for each highly attenuating material prior to generating the projection data.

11. A method in accordance with claim 1 further comprising the step of scaling the error-only image data for each highly attenuating material.

12. A method in accordance with claim 11 further comprising the step of generating a corrected image by adding the scaled error-only image data and the image data.

13. A method in accordance with claim 1 wherein the image data collected in the computed tomography system includes image data from a plurality of slices and wherein determining the attenuation characteristic for each highly attenuating material comprises the steps of:
   comparing image data from a first slice to image data from a second slice; and
   adjusting the attenuation characteristic for each highly attenuating material based on the comparison of the image data from the slices.

14. A method in accordance with claim 13 wherein adjusting the attenuation characteristic based on the comparison of the image data from the slices comprises the steps of:
   determining whether the variation between the first slice image data and the second slice image data is within a valid range; and
   if the variation is within the valid range, then adjusting the attenuation characteristic of the highly attenuating material.

15. A system for correcting for artifacts caused by highly attenuating objects in image data, the image data collected in a tomography scan, said system configured to:
   determine an attenuation characteristic for each material of the highly attenuating objects;
   identify the highly attenuating objects in the image data; and
   generate error-only image data for each high attenuating object.

16. A system in accordance with claim 15 wherein to identify highly attenuating objects, said system is configured to:
   segment the image data into material classes;
   generate a membership function for each material class.

17. A system in accordance with claim 15 wherein to generate error-only image data for each highly attenuating object said system is configured to generate a separate component image for each highly attenuating material.

18. A system in accordance with claim 17 wherein to generate the separate component images said system is configured to multiply the image data by each material class membership function.

19. A system in accordance with claim 17 wherein to generate error-only image data for each highly attenuating object, said system is configured to:
   generate projection data by forward projecting the component image of each highly attenuating material; and
   adjust the projection data to generate projection error data.

20. A system in accordance with claim 19 wherein to adjust the projection data to generate projection error data, said system is configured to adjust the projection data by the attenuation characteristic of each highly attenuating material.

21. A system in accordance with claim 20 wherein to adjust the projection data by the attenuation characteristic of each highly attenuating material, said system is configured to:
   use operator supplied data to identify the highly attenuating materials; and
   adjust the projection data by pre-defined attenuation characteristics based on the identified highly attenuating materials.

22. A system in accordance with claim 21 wherein to use the operator supplied data, the operator identifies the type of scan to be performed.

23. A system in accordance with claim 19 wherein to generate projection error data by adjusting the projection data, said system is configured to:
   filter the projection error data for each highly attenuating material; and
   backproject the filtered projection error data.

24. A system in accordance with claim 19 further configured to combine the projection data for each highly attenuating material prior to generating the projection data.

25. A system in accordance with claim 24 further configured to scale the error-only image data for each highly attenuating material.

26. A system in accordance with claim 25 further configured to generate a corrected image by adding the scaled error-only image data and the image data.

27. A system in accordance with claim 15 wherein the image data collected in the tomography scan includes image data from a plurality of slices and wherein to determine the attenuation characteristic for each highly attenuating material said system is configured to:
   compare image data from a first slice to image data from a second slice; and
   adjust the attenuation characteristic for each highly attenuating material based on the comparison of the image data from the slices.

28. A system in accordance with claim 27 wherein to adjust the attenuation characteristic based on the comparison of the image data from the slices, said system is configured to:
   determine whether the variation between the first slice image data and the second slice image data is within a valid range; and
   if the variation is within the valid range, then adjust the attenuation characteristic of the highly attenuating material.

29. A system in accordance with claim 15 further configured to generate a corrected image.

* * * * *

UNITED STATES PATENT AND TRADEMARK OFFICE
CERTIFICATE OF CORRECTION

PATENT NO.    : 6,035,012
DATED         : March 7, 2000
INVENTOR(S)   : Hsieh

It is certified that error appears in the above-identified patent and that said Letters Patent is hereby corrected as shown below:

<u>Title page,</u>
Item [73], insert the following:
-- [73] Assignee: General Electric Company, Schenectady, NY --

Signed and Sealed this

Twenty-second Day of October, 2002

Attest:

Attesting Officer

JAMES E. ROGAN
*Director of the United States Patent and Trademark Office*